United States Patent [19]

Hines et al.

[11] Patent Number: 5,456,118
[45] Date of Patent: Oct. 10, 1995

[54] GYRATORY COMPACTOR

[75] Inventors: Theodore G. Hines, Grove City; Roger A. Pyle, Clarion, both of Pa.

[73] Assignee: Pine Instrument Company, Grove City, Pa.

[21] Appl. No.: 198,497

[22] Filed: Feb. 18, 1994

[51] Int. Cl.⁶ .............................. G01N 3/08; G01N 3/24
[52] U.S. Cl. .............................................. 73/818; 73/843
[58] Field of Search ........................... 73/818, 790, 813, 73/789, 794, 795, 806, 807, 808, 811, 815, 816, 841, 842, 843, 845; D15/20

[56] References Cited

U.S. PATENT DOCUMENTS

| | | | |
|---|---|---|---|
| 2,972,249 | 2/1961 | McRae et al. | 73/794 |
| 2,980,978 | 4/1961 | Marshall | 73/811 |
| 3,374,665 | 3/1968 | Preston | 73/789 |
| 4,196,635 | 4/1980 | Zuber et al. | 73/794 |
| 4,942,768 | 7/1990 | McRae | 73/795 |
| 5,036,709 | 8/1991 | McRae | 73/841 |
| 5,046,367 | 10/1991 | Iizuka | 73/789 |
| 5,275,056 | 1/1994 | Hamilton et al. | 73/794 |

FOREIGN PATENT DOCUMENTS

| 1102536 | 5/1986 | Japan | 73/841 |
|---|---|---|---|
| 1118742 | 5/1989 | Japan | 73/818 |

Primary Examiner—Thomas P. Noland
Assistant Examiner—William L. Oen
Attorney, Agent, or Firm—Calfee Halter & Griswold

[57] ABSTRACT

A gyratory compacting apparatus for compacting a specimen of material subjected to pressure while gyrating the material includes a frame for supporting a mold, a mold gyrating carriage, a ram, and a ram driving assembly. The mold gyrating carriage receives a cylindrical mold having a cavity for holding material and an external peripheral flange about which the mold carriage is guided and driven to rotate to gyrate the mold while the ram is drivingly inserted through the open top of the mold. The ram driving assembly is supported by a flexible portion of the frame which flexes in reaction to force transferred by the ram. Strain gauges on the flexible portion of the frame provide feedback control data on ram force to an integrated computer control system which selectively controls the ram driving assembly to control the force transferred by the ram at least partially according to data generated by the strain gauges. The energy required to rotate the mold gyrating carriage around the mold is measured.

42 Claims, 8 Drawing Sheets

SPECIMEN HEIGHT (mm) vs. GYRATION NO.

Date: 12/20/93
Time: 13:40

|  : | 0 | 1 | 2 | 3 | 4 | 5 | 6 | 7 | 8 | 9 |
|---|---|---|---|---|---|---|---|---|---|---|
| 0 : | 126.0 | 122.2 | 120.3 | 118.8 | 117.8 | 116.9 | 116.1 | 115.5 | 114.9 | 114.4 |
| 10 : | 113.9 | 113.5 | 113.1 | 112.8 | 112.5 | 112.2 | 111.9 | 111.6 | 111.4 | 111.2 |
| 20 : | 111.0 | 110.8 | 110.6 | 110.4 | 110.2 | 110.0 | 109.9 | 109.7 | 109.6 | 109.4 |
| 30 : | 109.3 | 109.2 | 109.0 | 108.9 | 108.8 | 108.7 | 108.6 | 108.5 | 108.4 | 108.3 |
| 40 : | 108.2 | 108.1 | 108.0 | 107.9 | 107.8 | 107.8 | 107.7 | 107.6 | 107.5 | 107.4 |
| 50 : | 107.4 | 107.3 | 107.2 | 107.2 | 107.1 | 107.0 | 107.0 | 106.9 | 106.9 | 106.8 |
| 60 : | 106.8 | 106.7 | 106.7 | 106.6 | 106.6 | 106.5 | 106.5 | 106.4 | 106.4 | 106.3 |
| 70 : | 106.3 | 106.2 | 106.2 | 106.1 | 106.1 | 106.1 | 106.0 | 106.0 | 105.9 | 105.9 |
| 80 : | 105.9 | 105.8 | 105.8 | 105.8 | 105.7 | 105.7 | 105.6 | 105.6 | 105.6 | 105.5 |
| 90 : | 105.5 | 105.5 | 105.4 | 105.4 | 105.4 | 105.3 | 105.3 | 105.3 | 105.3 | 105.2 |
| 100 : | 105.2 | 105.2 | 105.2 | 105.1 | 105.1 | 105.1 | 105.1 | 105.0 | 105.0 | 105.0 |
| 110 : | 105.0 | 104.9 | 104.9 | 104.9 | 104.9 | 104.8 | 104.8 | 104.8 | 104.8 | 104.8 |
| 120 : | 104.7 | 104.7 | 104.7 | 104.7 | 104.7 | 104.6 | 104.6 | 104.6 | 104.6 | 104.5 |
| 130 : | 104.5 | 104.5 | 104.5 | 104.5 | 104.5 | 104.5 | 104.4 | 104.4 | 104.4 | 104.4 |
| 140 : | 104.4 | 104.3 | 104.3 | 104.3 | 104.3 | 104.3 | 104.3 | 104.2 | 104.2 | 104.2 |
| 150 : | 104.2 | 104.2 | 104.2 | 104.1 | 104.1 | 104.1 | 104.1 | 104.1 | 104.1 | 104.0 |
| 160 : | 104.0 | 104.0 | 104.0 | 104.0 | 104.0 | 104.0 | 103.9 | 103.9 | 103.9 | 103.9 |
| 170 : | 103.9 | 103.9 | 103.9 | 103.9 | 103.8 | 103.8 | 103.8 | 103.8 | 103.8 | 103.8 |
| 180 : | 103.8 | 103.8 | 103.8 | 103.8 | 103.7 | 103.7 | 103.7 | 103.7 | 103.7 | 103.7 |
| 190 : | 103.7 | 103.7 | 103.7 | 103.6 | 103.6 | 103.6 | 103.6 | 103.6 | 103.6 | 103.6 |
| 200 : | 103.6 | | | | | | | | | |

SAMPLE NO. : _____
SAMPLE SIZE: 150 mm
PRESSURE: 0.40 MPa
FINAL HT.: 103.4 mm
WEIGHT: _____
VOLUME: _____
SPEC. GRAV.: _____
VOIDS: _____
AGGREGATE: _____
GRADE ASPHALT: _____
% ASPHALT: _____
TEMPERATURE: _____

PASSING
200 _____
100 _____
50 _____
30 _____
16 _____
8 _____
4 _____
3/8 _____
1/2 _____
3/4 _____
1-1/2 _____

LAB. NO.: _____
REPORT BY: _____

| | No. Gyr. | % Air Voids |
|---|---|---|
| Init.: | _____ | _____ |
| Design: | _____ | _____ |
| Final: | _____ | _____ |

FIG 7

GYRATORY COMPACTOR

FIELD OF THE INVENTION

The present invention relates generally to a method and apparatus for testing materials and, in particular, to a method and apparatus for testing paving materials by compaction and gyration.

BACKGROUND OF THE INVENTION

Materials testing machines for simulating actual forces upon materials, such as the forces of vehicular traffic upon an asphalt surface of a road bed, have been devised to produce a sample of material which evidences the physical effects of repeated loading by for example compression, compaction, shear strain, plane-strain, and thermal reactivity. Such machines typically include a material holding mold which is inserted into a chamber or carriage which positions the mold for insertion of a ram into the mold cavity to compress the material in the mold. The mold may be gyrated about a small angle relative to the vertical axis of the ram, by motion of the mold carriage, as the material is compressed by the ram to simulate actual forces on the material in the application environment.

U.S. Pat. No. 2,972,249 discloses a kneader compactor which uses opposed plungers to compress materials within a mold chuck mounted for gyratory oscillation to produce kneading stresses in the material in the mold. Gyration of the mold as the material is compressed produces relative motion of particles of the material which simulates the physical response of asphalt material to vehicle load forces.

U.S. Pat. Nos. 4,942,768 and 5,036,709 disclose a paving material testing machine in which paving material to be tested is placed in a mold held by a chuck which is gyrated about a vertical axis while the material is compressed in the mold from the bottom by a hydraulically driven ram. As the mold chuck is rotated, a portion of the mold chuck in contact with the mold dynamically influences the axially adjustable chuck so that deformation of the material within the mold induced by the gyration changes the angle of gyration. This subjects the material in the mold to a gyratory kneading action analogous to the forces exerted by vehicles moving over asphalt surfaces. The machine also performs cyclic vertical loading by timed control of predetermined applied forces of the hydraulic ram upon the sample to simulate the flexing forces of vehicle tires rolling upon the asphalt surface.

Accurate calibration, control and monitoring of the compressive load of the ram upon a sample within the mold as the mold is gyrated is critical to obtaining accurate test results, i.e., compacted specimens which have specified densities, substantially uniform alignment of aggregate materials mixed with the specimen, and elastic properties which closely approximate real world applications. Precise control of the linear travel and compressive force of hydraulically driven rams in compaction devices requires the use of comparatively expensive control components. Also, hydraulic systems are heat sensitive and require frequent maintenance of seals and fluid.

The angle of gyration of the mold during compaction is also a critical factor which determines the amount of kneading action with resultant shear stress and strain of the material within the mold. Although the prior art devices induce kneading action of the material within the mold, the angle of gyration as determined by the density and flow of the material adds a variable which complicates accurate interpretation of the test results. Prior gyratory compaction testing machines do not provide for a precisely fixable and adjustable angle of gyration.

Automated control and safety of operation of gyratory compactors, each vital to obtaining accurate tests results without extensive operator training, are features not adequately addressed in the design of prior machines.

SUMMARY OF THE INVENTION

The present invention provides an improved apparatus and method for preparing a specimen of compressed material by gyratory compaction wherein the angle of gyration is precisely fixed, and the compressive force of the compaction ram upon the material is precisely determinable and controlled throughout the compaction process. The operations of the gyratory compactor of the present invention are controlled by a fully integrated computer control system which controls compaction pressure, gyration cycles and rate, and ram travel to produce compacted material specimens by a predetermined number of gyration cycles or a predetermined compacted specimen height. A stepping motor/load beams feedback drive system integral with a lead screw driven compaction ram provides precision linear control of ram travel and pressure relative to the specimen to be compacted. A completely enclosed compacting chamber and simplified control panel allow the compactor to be safely operated and without extensive operator training.

In accordance with one aspect of the invention, a materials testing apparatus for subjecting a material to forces is provided which includes a mold for containing a quantity of material, a mold supporting frame in contact with a rotatable mold carriage also supported by the frame and connected to a mold carriage tilt assembly operative to lift a portion of the mold carriage to incline the vertical axis of the mold, means for rotating the mold carriage about the mold, and a material compaction ram connected to a ram driving assembly and drivingly insertable into the mold for exerting a compressive force upon material within the mold while the mold carriage is rotated about the mold.

In accordance with another aspect of the invention a gyratory compaction apparatus for subjecting a material to forces is provided which includes a mold having a mold cavity for receiving a quantity of material, the mold having an open top and a closed bottom, a ram axially inserted and driven into the mold cavity through the open top of the mold to compact the material in the mold cavity, and means for gyrating the mold while the ram is inserted and driven into the mold cavity.

In accordance with another aspect of the invention a material testing machine for applying a linear force to a material to be tested is provided. The machine includes a frame for supporting a guide for a ram, a ram driven for linear movement in the guide by an electrically powered motor, load beams as an integral part of the frame and supporting the ram driving lead screw, the load beams being flexible in reaction to forces transferred by the ram, means for measuring an amount of flexing of the load beams, and means for controlling a speed of the ram drive motor in response to measured values of flexion of the load beams.

To the accomplishment of the foregoing and related ends, the invention comprises the features hereinafter fully described and particularly pointed out in the following detailed description made with references to the annexed drawings which set forth in detail certain illustrative embodiments of the invention, these being indicative, however, of but a few of the various ways in which the invention may be employed.

BRIEF DESCRIPTION OF THE DRAWINGS

In the annexed drawings:

FIG. 7 is a representation of a printout of compaction data acquired by the control system.

DESCRIPTION OF PREFERRED EMBODIMENTS

Figure 1:
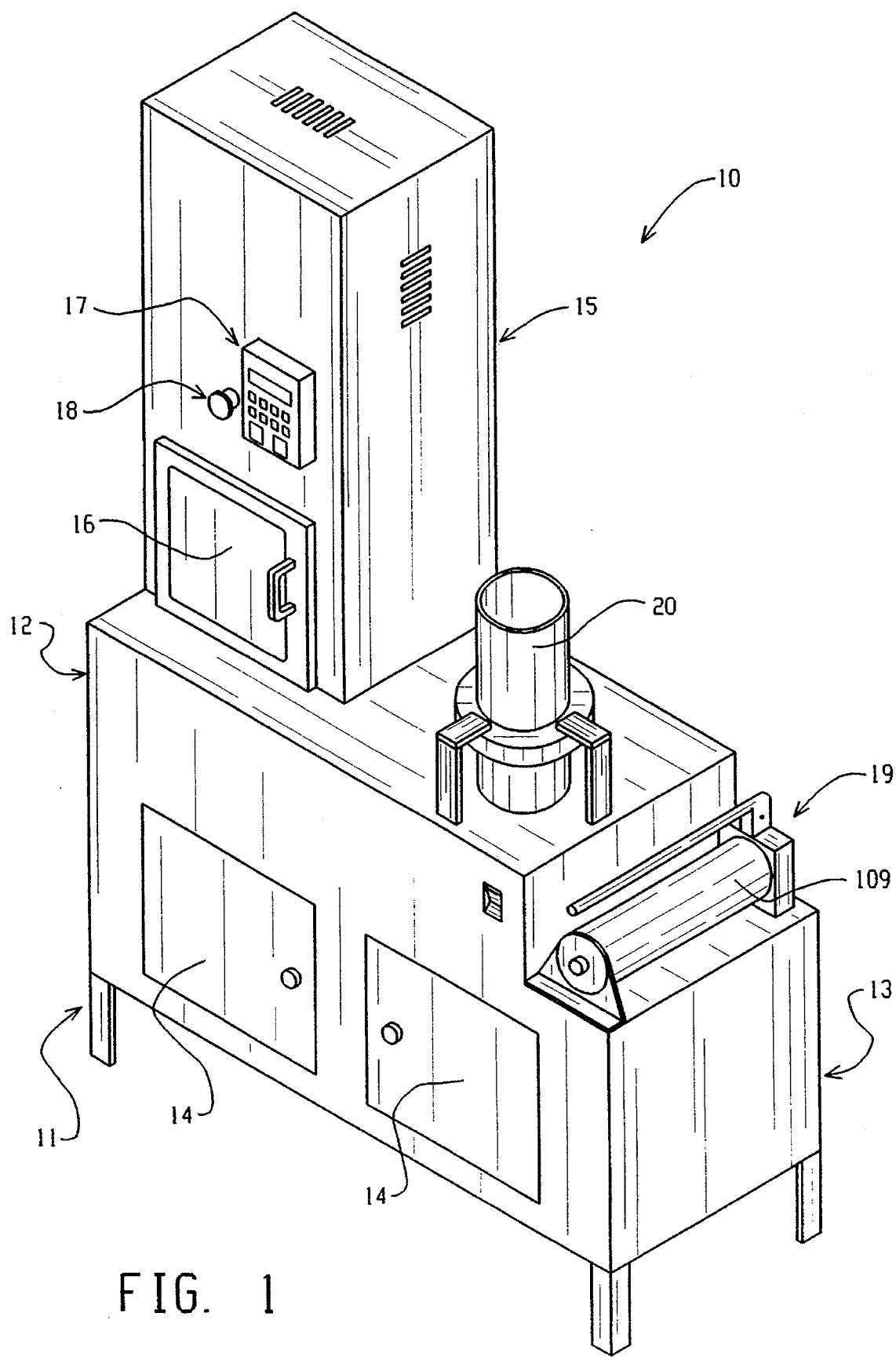
FIG. 1 is a schematic illustration of a gyratory compactor of the present invention as housed in a cabinet.

With reference to FIG. 1, a gyratory compactor is indicated generally at 10. A frame 11 supports the compactor and peripheral components, housed in protective a cabinet 12 attached to the frame. The frame 11 includes a lower portion 13 having storage area access doors 14, and an upper portion 15 having an access door 16 to a specimen mold receiving portion of the compactor. A control panel 17 for controlling the operations of the compactor, and an emergency stop button 18, are mounted upon the exterior of upper portion 15. An extruder, indicated generally at 19, for extruding a compacted specimen from a mold as described below, is mounted in the base portion of the frame.

Figure 2:
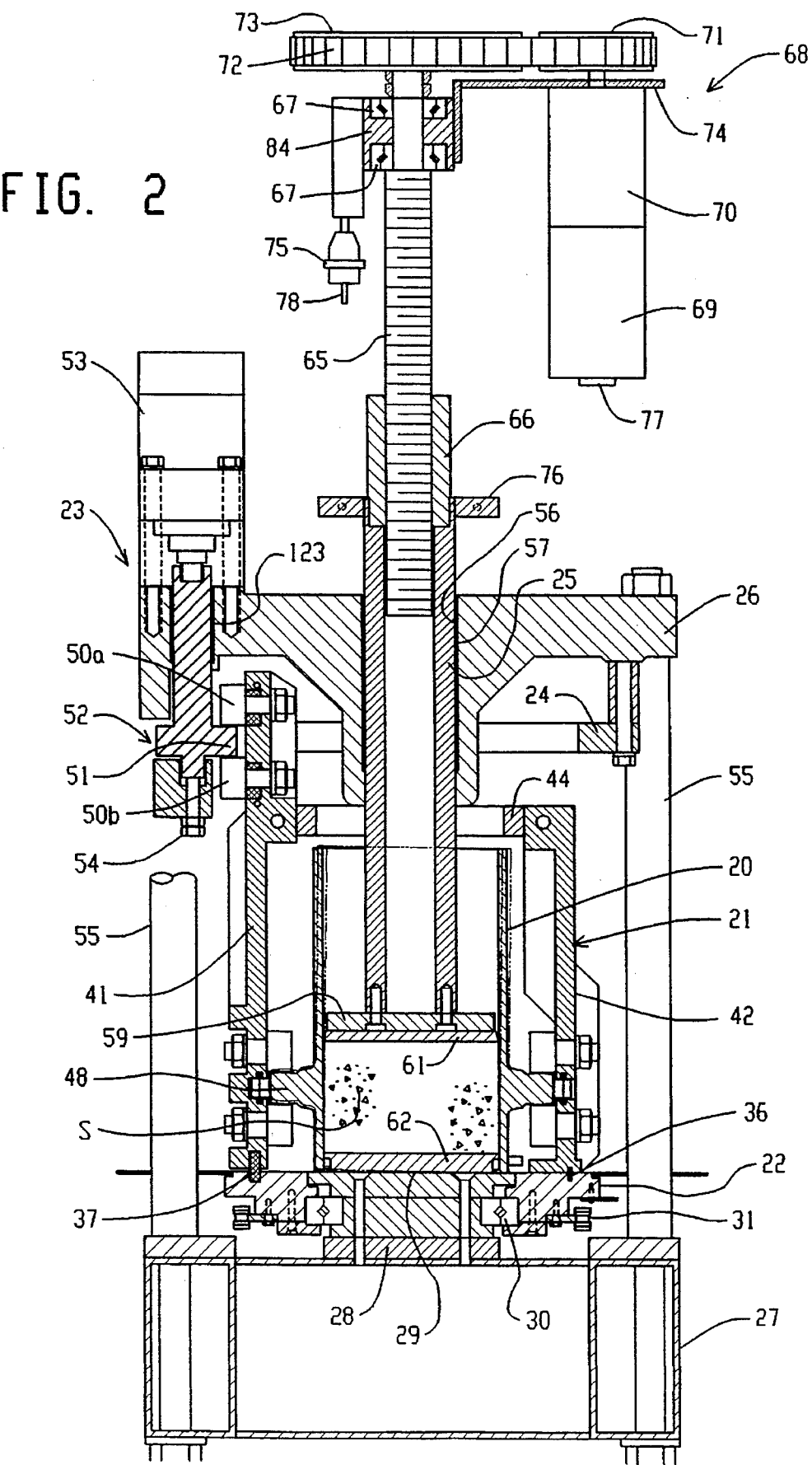
FIG. 2 is a cross-sectional view of a portion of a gyratory compactor of the present invention.

Referring additionally to FIG. 2, there is illustrated in cross-section the specimen compacting portion of gyratory compactor which is housed in upper portion 15 shown in FIG. 1. In general, the major components of the compacting portion of the apparatus include a generally cylindrical mold 20 (into which a material specimen S is placed) surrounded by a mold carriage assembly 21 connected at a bottom end to a circular rotation base 22 and in roller guided contact at a top end with a mold carriage tilt link assembly 23 for aligning upper rollers of the mold carriage assembly for rotation about a fixed ring 24. A ram 25 is positioned vertically through a guide frame 26 for insertion into mold 20 to compress material specimen S.

A base frame 27 (connected to frame 11 of lower portion 13 of FIG. 1) supports a mold base 28 which provides a horizontal surface 29 upon which the mold 20 is placed during gyratory compaction of material in the mold. The mold base 28 supports and is encircled by a rotation base bearing 30 connected to circular rotation base 22. The rotation base bearing 30 may be for example a crossed roller bearing of sufficient load rating to withstand the reaction force through the mold carriage at maximum gyration rpm of a fully loaded mold as described below.

Figure 3:
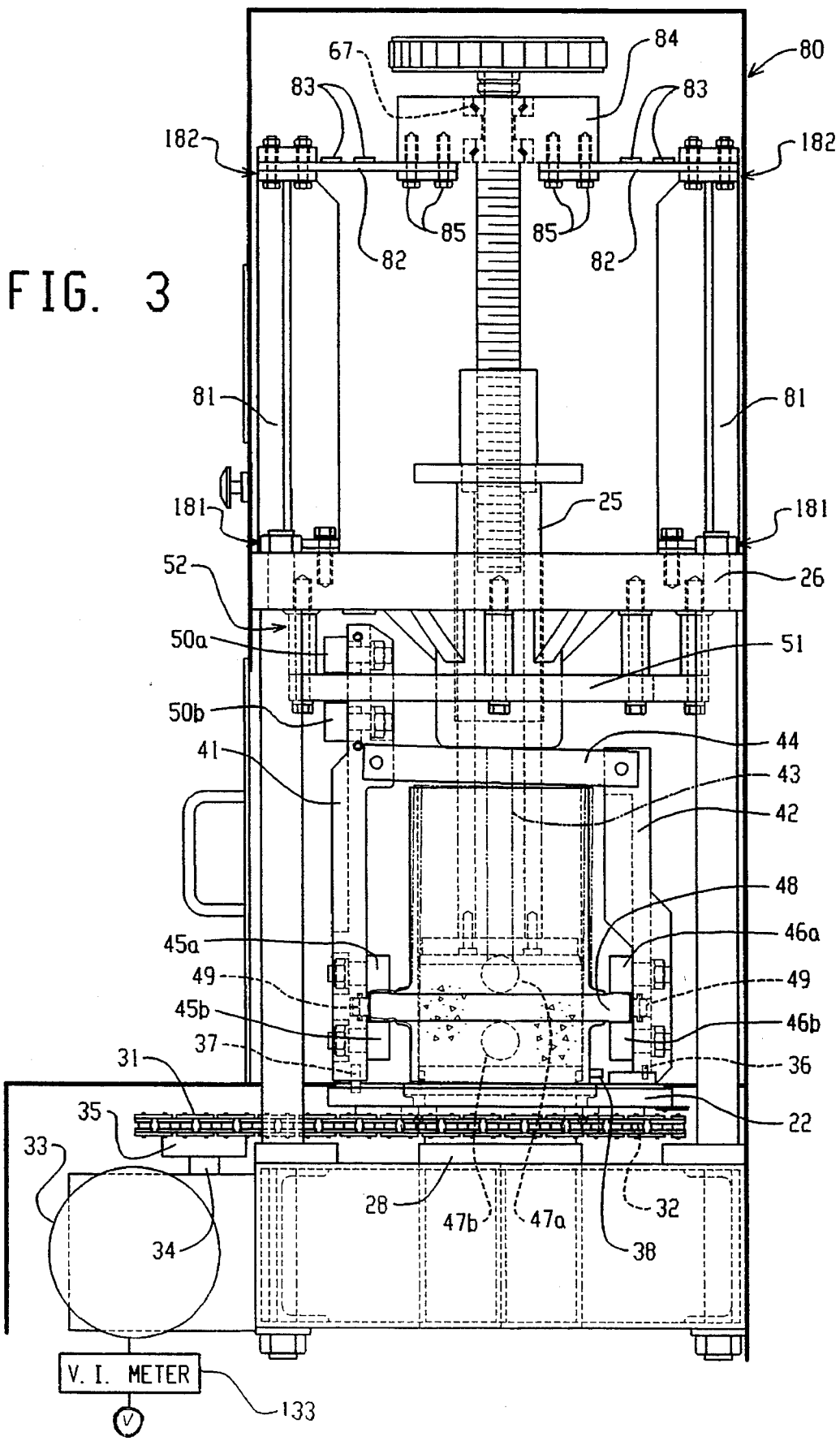
FIG. 3 is a side view of the compacting portion of the gyratory compactor of the present invention with the cabinet wall removed.

As further illustrated in FIG. 3, a drive chain 31 engaging a sprocket 32 attached to rotation base 22 (parallel to the plane of rotation) rotationally drives rotation base 22 upon rotation base bearing 30 about mold base 28. An electric drive motor 33 is powered to rotate shaft 34 to rotate drive sprocket 35 in engagement with drive chain 31. By attachment of a bottom end of mold carriage assembly 21 to rotation base 22 (by fasteners 36 and pins 37), the chain driven rotation of mold base 28 rotates the entire mold carriage assembly 21 around mold 20, without rotating mold 20.

Figure 4:
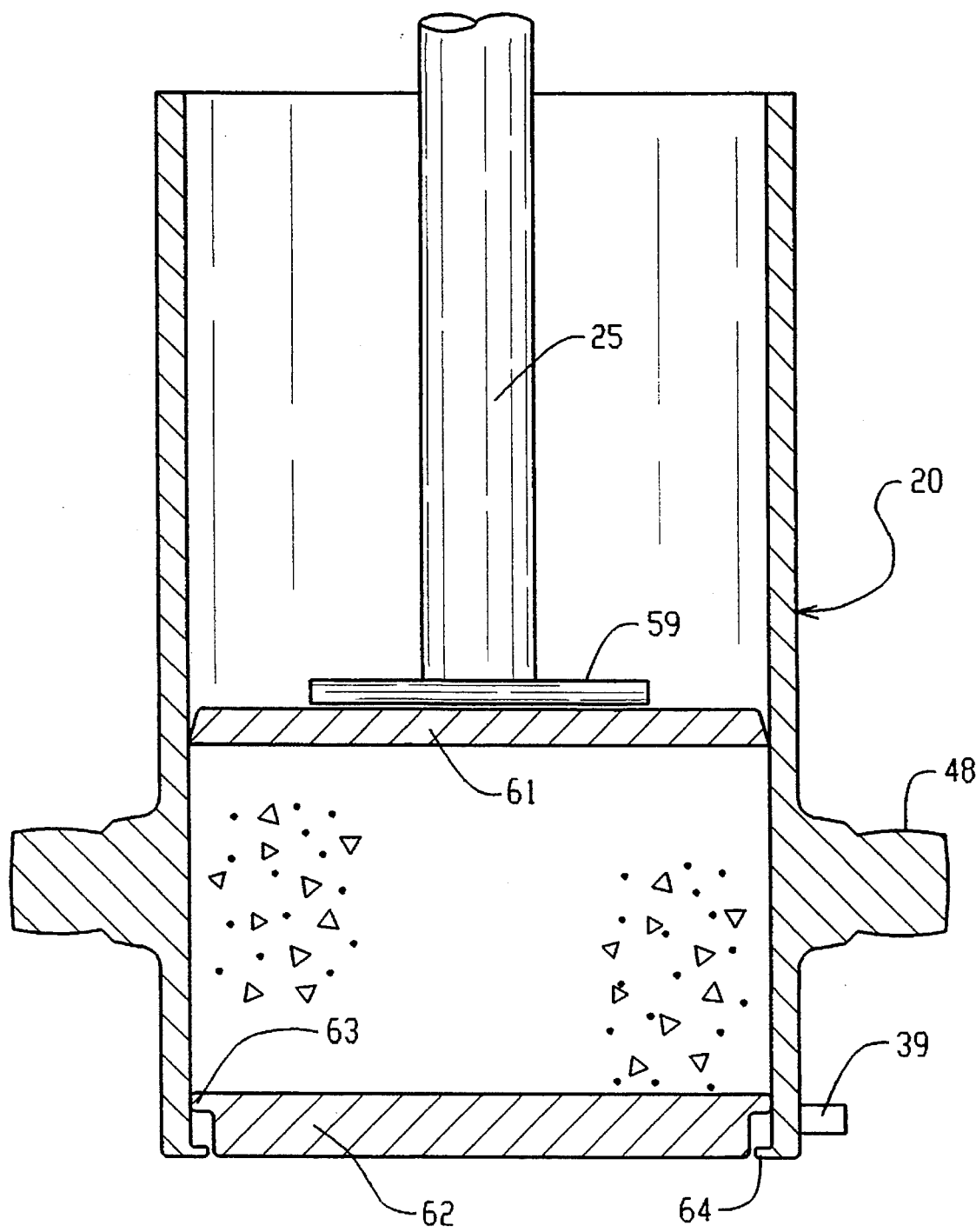
FIG. 4 is a cross-sectional view of the mold assembly of the present invention.

A chuck 38 may be provided to protrude upward from horizontal surface 29 of mold base 28 to contact a key 39 extending from the side of mold 20 (as shown in FIG. 4) to insure against any frictionally induced rotation of mold 20 during gyration which would interfere with testing requiring an exact number of gyrations.

The primary function of mold carriage assembly 21 is to gyrate the vertical axis of the mold 20 about the vertical axis of the ram 25 during compaction of material in the mold by the ram. As best shown in FIG. 2, mold carriage assembly 21 includes at least two vertical members 41 and 42, suspended by through pin attachment from a mold carriage ring 44 at opposing points on the ring. A third vertical member 43 (shown in phantom in FIG. 3) may also be provided equidistant from members 41 and 42 to maintain intersection of the vertical axis of the mold with the apex of gyration and precisely maintain the angle of gyration during rotation of rotation base 22. Vertical members 41 and 42 and 43 each support, by horizontal journalled bearings, parallel vertically spaced apart mold roller sets 45a and 45b, 46a and 46b and 47a and 47b, respectively, which receive and support a radial flange 48 attached to and extending horizontally from the outer periphery of mold 20. Each vertical member may also have a vertically mounted roller 49 placed between each of the spaced apart roller sets for rolling contact with the outer peripheral face of radial flange 48 of mold 20 to reduce wear and friction of the mold during gyration.

To offset the vertical axis of the mold 20 within the mold carriage assembly to a selected gyration angle, vertical member 41 serves as mold carriage lift link, having an upper set of parallel spaced apart rollers 50a and 50b straddling a ring section 51 of a lift link 52 of the mold carriage tilt link assembly 23. Because ring section 51 constitutes a radial section of fixed ring 24, upper rollers 50 can travel about fixed ring 24 only when lift 52 is raised to align ring section 51 in the same plane as fixed ring 24. Lift link 52 is actuated to perform this alignment function by, for example, a hydraulic cylinder 53, which can be optionally equipped with a self-locking check valve. With fixed ring 24 positioned in a plane parallel to horizontal surface 29 of mold base 28, lifting of vertical member 41 by mold carriage tilt link assembly 23 to align ring section 51 with fixed ring 24, the vertical axis of the mold 20 in the mold carriage is tilted to a gyration angle as determined by the length of vertical member 41. Driven rotation of rotation base 22 rotates the mold carriage 21 and roller sets 45, 46, 47 about radial flange 48 of the mold, and upper roller set 50 about fixed ring 24. Roller sets 45 and 47, being partially lifted by the tilt link assembly, position radial flange 48 of mold 20 in a plane not parallel to horizontal surface 29, i.e., with the vertical axis of the mold positioned at an angle out of co-axial alignment with the vertical axis of the ram (as indicated in FIGS. 2 and 3) thereby positioning the mold for gyration about the foot of the ram.

Figure 5A:
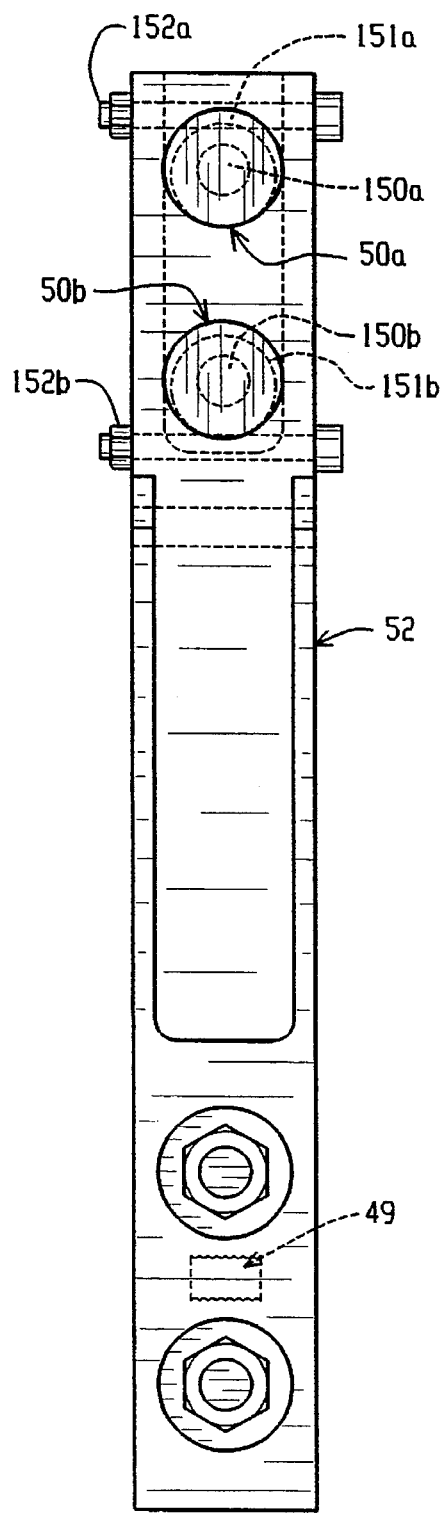
FIG. 5A is a side view of an adjustable lift link assembly of the mold carriage of the present invention, taken in the direction of the arrows 5A—5A in FIG. 5B.
Figure 5B:
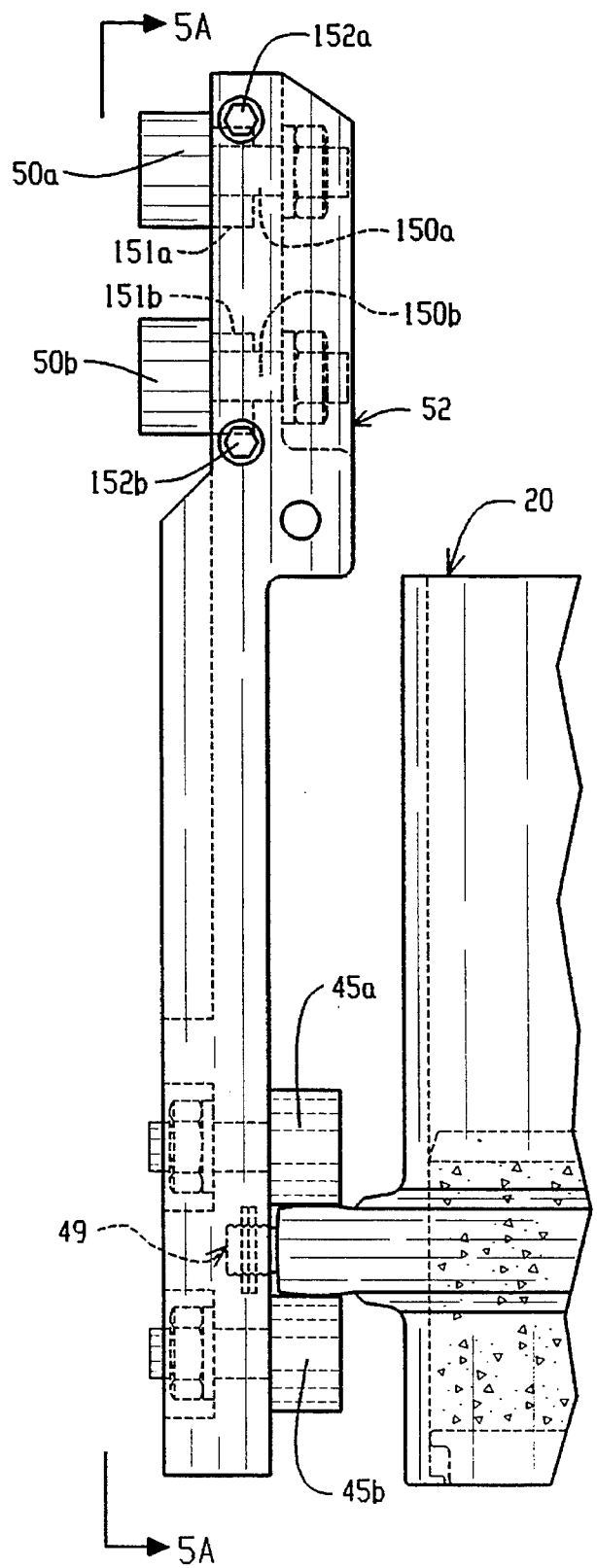
FIG. 5B is a front view of the adjustable lift link assembly of the present invention.

To enable fine adjustment of the gyration angle of the mold within the mold carriage assembly after alignment of ring section 51 with fixed ring 24, vertical member 41 can be adapted to include axis adjustable mounting of upper roller set 50 to selectively adjust the distance between the axes of upper roller set 50 and lower roller set 45. As shown in FIGS. 5A and 5B, shafts 150a and 150b of upper rollers 50a and 50b are each eccentrically mounted within respective cams 151a and 151b, each having worm-screw threads about their periphery and mounted within lift link 52 to be in threaded engagement with corresponding cam adjustment worms 152a, 152b also mounted within lift link 52 transverse to the axes of cams 151.

In operation, for example to change the distance between the axis of upper roller 50a and lower roller 45a, cam adjustment worm 152a is turned to rotate by worm screw engagement cam 151a which carries the axis of upper roller shaft 150a about a circular path offset for example one eighth of one inch from the axial center of cam 151a. Cam adjustment worm 152b is then turned to rotate cam 151b to bring roller 50b into contact with the underside of fixed ring 24.

Fine pitch threads in the worm screw engagement of worms 152 with cams 151 provides for minute positional adjustment of the axes of upper rollers 50 relative to the axes of lower rollers 45 within the range of the offset between axes of the cams and upper rollers. The cam adjustment mechanism therefore provides for fine gyration angle adjustment within, for example, a one and one half degree range provided by the cam/roller axes offset, to adjust and fix the gyration angle of the mold within the mold carriage. An exact gyration angle within the cam adjustment range is determinable by use of a mold jig and clinometer positioned within the mold carriage. When a desired gyration angle is set by worms 152, a hydraulic stop 54 is adjusted and set to define a linear travel distance of lift link 52 (as actuated by hydraulic cylinder 53) which corresponds to the length of vertical member 41 for return of the mold carriage and mold to a zero degree gyration angle position.

As shown in FIG. 2, fixed ring 24 is attached to guide frame 26 positioned and supported above the mold carriage assembly 21 by tie rods 55 connected to base frame 27. Guide frame 26 includes a vertical passage 123 for linearly guiding lift link 52 along its vertical axis as actuated by vertical hydraulic cylinder 53 fixedly mounted to the top of guide frame 26. Guide frame 26 further includes a central vertical passage 56 lined with a ram sleeve bearing 57 for receiving and guiding a ram 25 linearly along a vertical axis into the open top of mold 20. A ram foot 59, of a diameter less than the internal diameter of mold 20, is attached to the axial end of ram 25 inserted into the mold for compressive contact with a mold top plate 61 which is placed directly on top of the material specimen S in the mold. The diameter of ram foot 59 may be less than the diameter of mold top plate 61 which, in addition to insulating a heated material specimen from heat loss, acts to evenly distribute the compressive consolidation force of the ram foot across the width of the specimen in the mold. The diameter of the mold top plate 61 is preferably made to close tolerance with the internal diameter of the mold, to cover the entire specimen with only minor contact of the edges of the mold top plate with the interior walls of the mold during gyratory compaction. By this arrangement, the smaller diameter of the ram foot avoids contact of the peripheral edges of the ram foot with the walls of the mold during gyration. The ram foot 59 is detachable from the end of the ram for exchange with a smaller diameter ram foot used in connection with a smaller diameter mold. Molds of different cavity dimensions (diameters) can be used with the compactor provided the radial flange 48 is a constant diameter to fit within the roller sets of the mold carriage.

As shown in FIG. 4, the material in the mold is compacted by the ram foot 59 and the mold top plate 61 against a removable mold bottom plate 62 which is retained in the bottom of the mold 20 by contact of a radial flange 63 of mold bottom plate 62 with an annular lip 64 projecting radially inward at the bottom of mold. This structure, in combination with the position of radial flange 48 relative to the mold, optimizes the geometry near the bottom of the mold where the majority of compaction takes place, allowing the mold to gyrate about the mold bottom plate 62 which remains flush upon horizontal surface 29 as shown in FIG. 3, thus minimizing relative motion and wear between the mold bottom plate 62 and horizontal surface 29 of mold base 28. Hard self-lubricating surfaces are used on the interfacing areas of the mold assembly to reduce wear.

Referring again to FIGS. 2 and 3, ram 25 is driven linearly along its vertical axis by a lead screw 65 threaded through a lead screw nut 66 fixed to a top end of ram 25. The top end of lead screw 65 is supported and journalled to rotate within lead screw thrust bearings 67 mounted within a block 84 supported by an upper frame portion indicated in FIG. 3 generally at 80. A lead screw drive assembly, indicated generally at 68, includes an electric stepping motor 69, such as Model #UPD 5913 manufactured by Oriental Motor Corporation U.S.A., coupled to a gear reducer unit 70 which is supported by a bracket 74 attached to block 84. A drive gear 71 is attached to a shaft output of gear reducer unit 70 and engaged by a toothed drive belt 72 also engaged with a lead screw drive gear 73 attached to the top end of the lead screw above lead screw thrust bearings 67. A linear position sensor 75, such as for example a linear potentiometer, is mounted to block 84 for positioning proximate and parallel to the lead screw. A ram position indicator arm 76 extending laterally from the top end of the ram 25 moves the mechanical slide 78 of the potentiometer which provides an electrical signal to the control circuitry indicating a home position of the ram. A rotary encoder 77 connected to stepping motor 69 provides (through a control system described below) a digital indication of linear travel of the ram according to the known pitch of the lead screw. By feedback loop control of power to stepping motor 69 as described below, the linear position of the ram foot relative to horizontal surface 29 of mold base 28 can be precisely determined, controlled and monitored. This allows the compactor to be programmed to, for example, compact a specimen to a predetermined height which corresponds to a calculated desired air void (i.e., density).

The upper frame portion 80, which supports the lead screw drive assembly 68, block 84 and thrust bearings 67, is constructed as an integral part of the entire frame structure of the compactor. As shown in FIG. 3, upper frame portion 80 includes vertical members 81 secured at a bottom end 181 to the top of guide frame 26 and supporting at a top end 182 outboard ends of horizontal load beams 82 attached at inboard ends to block 84 by fasteners 85. Load beams 82 are designed to flex in response to the stresses which result when force is applied by the ram to a specimen in the mold. Redundant strain gauges 83 are applied to surfaces of load beams 82 to detect the strain which results from deflection of the load beams in response to the force being applied by the ram. The relative positions of the block 84, as supported by load beams 82, and the lead screw drive assembly 68, as supported by bracket 74 attached to block 84, in combination with the placement of strain gauges 83 upon surfaces of load beams 82, is designed to minimize the effect of the reactive forces from the lead screw drive assembly upon accurate measurement by the strain gauges of the linear force of the ram. Strain gauges 83 provide an analog signal indicative of the magnitude of deflection of the beams and, correspondingly, the axial force of the ram foot upon the specimen. By operation of the feedback loop control system described below, data received from strain gauge measurements is used to determine pulse application to stepping motor 69 to, for example, maintain a constant consolidation pressure of the ram upon the specimen, or otherwise control ram pressure or position in any mode desired.

The amount of energy required to gyrate and compact aggregate asphalt mixes varies dependent in part upon the viscosity of the asphalt oil and the type and shape of mixed aggregate. Therefore, a measurement of an amount of energy required to gyrate an aggregate asphalt mix sample undergoing compaction can yield useful data on physical properties of the asphalt mix. To enable measurement of an amount of energy required to gyrate the mold about the compacting ram, sensors may be provided in the mold base drive train assembly. For example, a power measurement device 133 such as a watt meter, capable of measuring voltage and current, may be provided at the power input to electric drive motor 33 to provide a measurement of an amount of power input to the motor. The analog value of this measurement can then be calibrated by an absorption dynamometer (such as a prony brake which applies a known frictional load) to factor out mechanical losses in the system to yield an accurate value of an amount of effort required to gyrate the mold in the gyratory compaction process.

Figure 6:
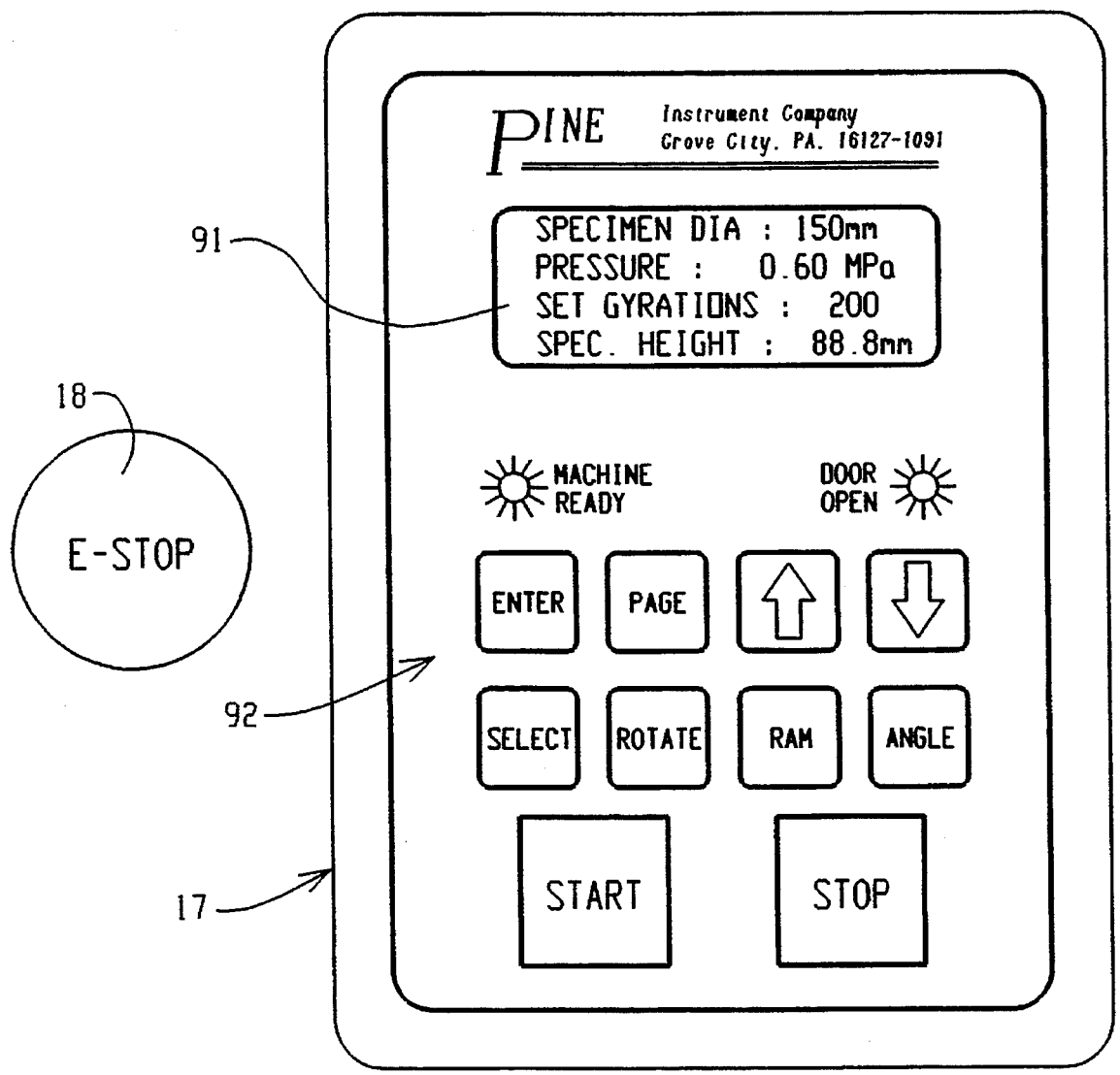
FIG. 6 is an illustration of the control panel layout of the gyratory compactor of the present invention.

A fully integrated interactive computer control system is provided to control the parameters of the various operations of the gyratory compactor. FIG. 6 illustrates the face of control panel 17 as mounted on the exterior of the compactor, which includes a screen display 91, such as an illuminated liquid crystal display, multiple touch pad entry keys 92 including START and STOP functions, and indicator lights such as "MACHINE READY" and "DOOR OPEN". As set forth in Table I, representative testing parameters and functions which can be input through the control panel include rotation of the mold carriage (by powered rotation of the mold base for example to a home position where the mold carriage opening between vertical members 41 and 42 is aligned with access door 16), manual control of ram position, actuation of the mold carriage tilt link assembly to adjust the mold to the desired gyration angle, consolidation pressure, specimen size, and number and rate (rpm) of gyratory revolutions.

TABLE I

| Key | Action |
| --- | --- |
| Page + ↑ | Moves to other options menu |
| Page − ↓ | Exits other option menu |
| Select | Selects parameter to be changed (value flashes) |
| ↑ or ↓ | Used to change value of flashing parameter |
| Enter | Stores changed parameters |
| Rotate | Display rotational status |
| Rotate & ↑ or ↓ | Rotates mold carriage |
| Ram | Display ram status |
| Ram & ↑ or ↓ | Move ram up or down |
| Angle | Display mold carriage angle status |

TABLE I-continued

| Key | Action |
| --- | --- |
| Angle & ↑ or ↓ | Toggles between 0 and gyration angle |
| Start | Starts test sequence |
| Stop | Pauses test |
| Enter and start | Automatic machine parking |

In an automated mode, control system software automatically calculates the force required to produce the desired consolidation pressure on the specimen being compacted. Data on compaction progress is then displayed on screen 91. Once an automated test routine is started parameters may be viewed but not changed. Data from the previous five (5) compaction tests is stored in volatile memory for purposes of, for example, producing a printout such as represented by FIG. 7, showing specimen height vs. gyration number for one compaction run and, in columnar form at the bottom additional data such as specimen size, ram pressure, etc. Of course all such data could be arranged in any chosen format.

Figure 8:
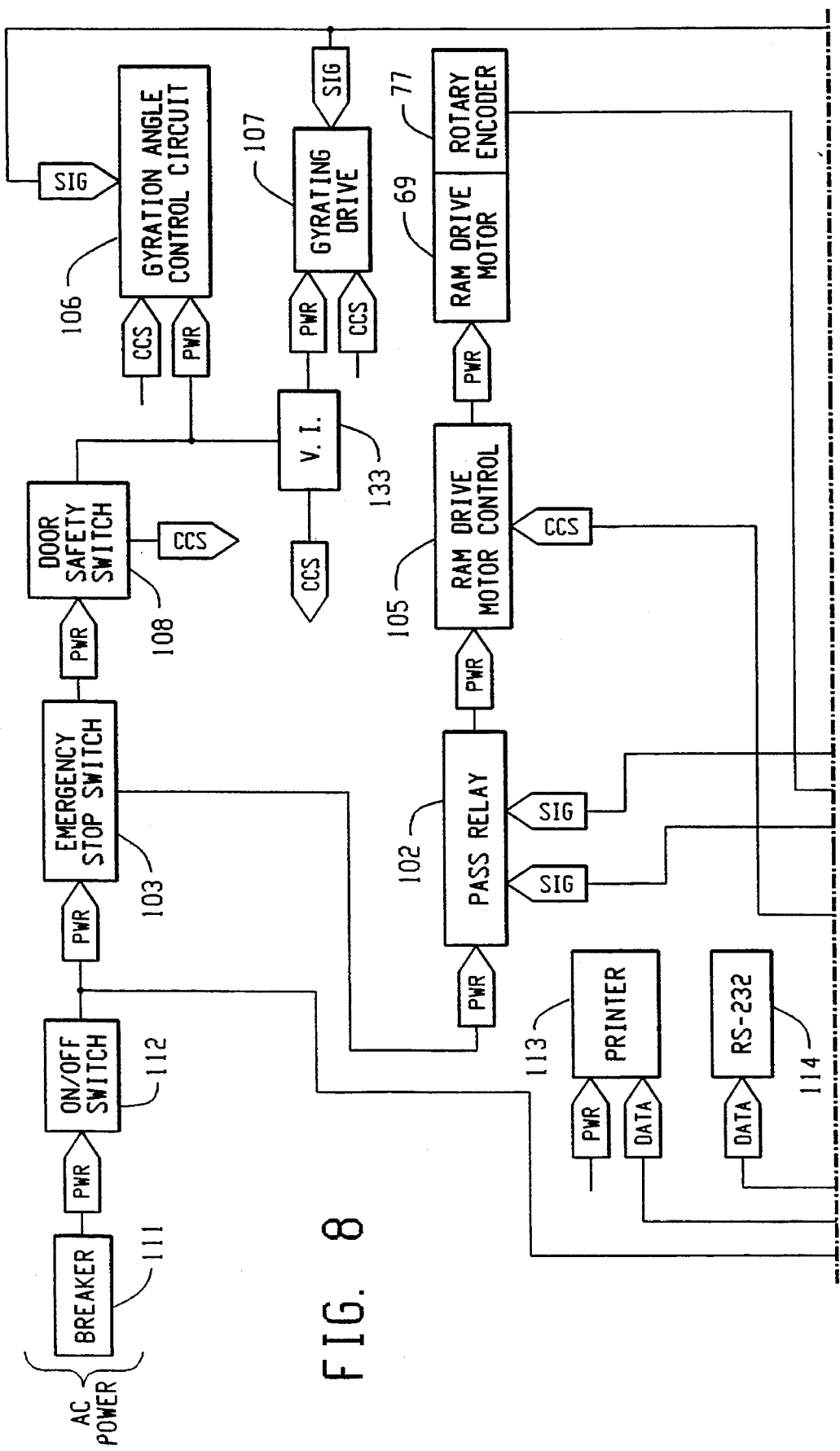
FIG. 8 is a schematic control diagram of the electronic computer control system of the gyratory compactor of the present invention.

FIG. 8 sets forth a simplified control diagram of the power and control system of the gyratory compactor which includes a central computer control system (CCS) 95 (including a CPU 104) for receiving and processing signals and data to control the operations of the compactor. For example, amplified signals from strain gauges 83 are sent through signal conditioner 88 for conversion to digital form by an A/D converter 96 for input into the CCS 95. The CCS uses this data, for example, to generate a signal to a ram drive motor control 105 to ram drive motor 69 to maintain a constant consolidation pressure exerted by the ram foot on the specimen within a preselected range by use of a modified proportional-integral-derivative algorithm which calculates the required output for the ram drive motor. The CCS also receives signals from rotary encoder 77 on the ram drive motor to generate a signal representing the corresponding ram movement and rate of movement for output to display 91. By counting the signals of the rotary encoder relative to a ram position detected by ram position sensor 75, the CCS can also determine the position of the ram foot from the horizontal surface of the mold base. Other inputs to the CCS include signals from a gyrating speed sensor 97, such as an optical sensor mounted proximate to the mold carriage, signals from a gyration angle sensor 98, and data signals input through control panel keypad 92. An over-pressure monitor 99 detects signals measured at the flexible portion of the frame which are beyond pre-specified parameters, such as would be detected with a firm object under the ram foot, to instruct the CCS to suspend further linear advancement of the ram by a signal to master pass relay 102. A gyration angle control circuit 106 and gyrating drive power controller 107 also receive a signal from over-pressure monitor 99 in the event of excessive ram force to prevent change of gyration angle and gyration of the mold during this condition to avoid damage to the machine. The magnitude of power supplied to the gyrating drive is measured by watt meter 133 which sends readings to the CCS. A door safety switch 108 disables power to the machine through the CCS to suspend all mechanical movement whenever the door 16 is open. AC power is supplied to the machine through a breaker 111 and switch 112. Data acquired by the CCS is output through appropriate ports to printer 113 and/or other peripheral device such as a monitor (not shown) through, for example, an RS-232 interface 114.

Accurate ram force data can be acquired and processed by the CCS by calibration of the compactor with a separate calibration kit. A preprogrammed calibration routine is reached through a special key sequence to prevent inadvertent use. This user friendly routine will allow a skilled technician to calibrate the machine with a minimum amount of training. Parameters calibrated include consolidation pressure as determined by ram force, specimen height, gyration angle, and the speed of gyration. Manual control of the system allows simple verification of calibrations without actual calibration of the compactor. Calibration data and date are stored in non-volatile computer memory. A precision non-contact tachometer can be used to verify the speed of gyration.

The linear force of the ram foot is calibrated with a ring dynamometer. The calibration routine prompts the operator to load the ring to a specific force, e.g., 2000N. The operator manually controls the ram to apply that forced as indicated by the ring dynamometer, and then presses "Enter". The CCS stores the required information and prompts the operator for the next predetermined load, and the process is repeated until the full range of the compactor has been calibrated. The operator may verify any of the calibrations before continuing by, for example, reapplying the force to the ring dynamometer. The calibration sequence will follow ASTM E4-89 procedures.

After the consolidation force has been calibrated over the entire force range of the machine, the operator follows a similar process to calibrate specimen height. The control system prompts the operator to insert a precision gauge block under the ram foot. The block is then loaded throughout the full force range applied by the ram foot, as may be automatically controlled by the CCS. Several gauge blocks are used to calibrate specimen height for the full range of ram travel. By loading through the entire operating range of the compactor while a gauge block is under the ram foot, accurate data on the internal frame deflection is obtained and recorded. The several gauge blocks representing different ram positions are use to create a matrix of data for compactor frame deflection at various loads and ram extension positions. This data is stored and utilized by the CCS during normal operation to eliminate errors in measurement due to compactor frame deflection.

Multiple safety features, such as an emergency stop switch, are incorporated into the design of the gyratory compactor including a completely enclosed compacting chamber which conceals all moving parts and pinch points. Compacting chamber access door 16 is provided with a lockout switch which disables the tilt, rotation and ram movement when the door is open. This lockout switch further utilizes a special keyed actuator which makes disabling of the switch difficult. The CCS monitors the status of the door and a light on the control panel indicates when the door is not latched. A window in the door allows the operator to view the compacting chamber.

The compactor further includes operation protection features integral to the control system to prevent or minimize damage to the compactor in the event of a failure. The over-pressure circuitry described in connection with FIG. 8 monitors the force of the ram independent of the software to ensure that the compactor is operating within its rated capacity. The compactor is structurally designed with inherent flexibility to withstand an overload of more than twice the maximum compacting force of the ram without damage. Limit switches are provided to indicate ram positions beyond normal travel. The control system can shut down the compactor through a master pass relay circuit 102 (shown in FIG. 8), as can the emergency stop switch 103 in the event of a potentially damaging condition. Independent circuitry (CPU watchdog 104) is provided to monitor the operation of the CCS to ensure proper function. The CCS can be programmed to generate error messages to aid in trouble shooting to quickly determine the cause of any problem. All critical systems have a built-in redundancy to prevent damage should a single failure occur.

By use of the above-described apparatus, a compacted specimen of hot mix asphalt (HMA) material (e.g., asphalt mixed with an aggregate material such as crushed stone) can be produced by loading a mold with a quantity of HMA material, placing the mold top plate on top of the material in the mold and putting the entire mold assembly into an oven for pre-compacting heating to a specified temperature, removing the mold assembly from the oven and placing it in the compacting chamber in position within the mold carriage. With the computer control system preprogrammed with testing parameters for constant compaction (consolidation) ram pressure, angle of gyration, number and rate of gyration or final specimen height within the mold (according to a predetermined air void percentage), the operator simply presses the start button and the CCS initiates the test routine by running the ram to contact with the mold top plate, tilting the mold carriage to the gyration angle, and commencing gyration and compaction at the specified rates. At completion of the test the mold carriage is actuated to return the mold to a zero degree gyration angle to square the specimen within the mold. The ram is then retracted to a home position to allow removal of the mold from the compactor. The mold is then placed in the extruder 19 which, by operation of hydraulic hand pump 109, drives a piston vertically upward against the mold bottom plate to push the specimen out of the mold.

Although the invention has been shown and described with respect to certain preferred embodiments, certain variations and modifications may occur to those skilled in the art. For example, many different types of motors and drive assemblies could be used to drive the various components of the gyratory compactor in connection with the computer control system to achieve constant consolidation compaction pressure at an exact gyration rate. The apparatus may be used to test materials other than asphalt and asphalt aggregates. The apparatus may also be used to perform applied force testing other than compaction or gyratory compaction. All such variations and modifications of the apparatus and method are within the purview of the present invention notwithstanding the defining limitations of the accompanying claims and equivalents thereof.

We claim:

1. A materials testing apparatus for subjecting a material to forces comprising, in combination, a frame for supporting a mold, a rotatable mold carriage having upper and lower rollers, said upper rollers engageable with a fixed ring fixedly attached to said frame, mold carriage rotation means, a mold carriage tilt link assembly, a ram, and a ram driving assembly, said mold having a cavity for containing a quantity of said material, said lower rollers of said rotatable mold carriage in contact with said mold, said upper rollers of said mold carriage in contact with said mold carriage tilt link assembly, said mold carriage tilt link assembly operative to lift a portion of said mold carriage by contact with said upper rollers of said mold carriage, whereby said mold carriage lifts said mold to tilt and fixedly position a vertical axis of said mold within said mold carriage, means for rotating said mold carriage about said mold, and a material compaction ram connected to a ram driving assembly, said ram drivingly insertable into said mold to exert a compressive force upon said material within said mold while said mold carriage is rotated about said mold.

2. The apparatus of claim 1 wherein said mold is generally cylindrical and has a flange extending radially outward from an outer periphery of the mold, wherein said flange is in contact with said lower rollers of said mold carriage.

3. The apparatus of claim 1 wherein a portion of said fixed ring is movable with said mold carriage tilt link assembly.

4. The apparatus of claim 1 wherein a portion of said mold carriage tilt link assembly is hydraulically operated.

5. The apparatus of claim 1 wherein said frame further includes a ram guide for guiding said ram along a vertical axis.

6. The apparatus of claim 1 wherein said ram driving assembly comprises, a lead screw journalled to rotate within lead screw bearings mounted within a lead screw bearing thrust block supported by said frame, said lead screw in threaded connection with a lead screw nut, said lead screw nut in contact with said ram, and a motor for powering rotation of said lead screw.

7. The apparatus of claim 6 wherein said motor for powered rotation of said lead screw is supported by attachment to said lead screw thrust bearing block.

8. The apparatus of claim 6 wherein said motor for powering rotation of said lead screw is an electric stepping motor.

9. The apparatus of claim 1 further comprising electrical means for measuring an amount of energy required to rotate said mold carriage about said mold.

10. The apparatus of claim 6 further comprising a rotary encoder operatively connected to said lead screw powering motor, said rotary encoder operative to provide an electrical signal indicative of axial rotation of a rotor of said motor.

11. The apparatus of claim 8 wherein said stepping motor is operative to drive said ram to maintain a constant compressive force of said ram upon said material within said mold as said material is compacted within said mold.

12. The apparatus of claim 8 wherein said motor is operative to maintain a constant compressive force of said ram without rotation.

13. The apparatus of claim 1 further including a ram home position sensor operative to sense a home position of said ram retracted from said cavity of said mold.

14. The apparatus of claim 1 wherein said frame further comprises a flexible portion which flexes in reaction to force transferred by said ram.

15. The apparatus of claim 14 wherein said lead screw bearing thrust block is supported by said flexible portion of said frame.

16. The apparatus of claim 15 further comprising at least one strain gauge applied to a surface of said flexible portion, said stain gauge operative to produce electrical signals indicative of a degree of flex of said flexible portion in response to force transferred by said ram.

17. The apparatus of claim 16 further comprising a control system operatively connected to said ram driving assembly for controlling linear motion of said ram in accordance with electrical signals representative of forces measured by said strain gauge.

18. The apparatus of claim 1 wherein said mold carriage tilt link assembly further comprises an adjustable link for positionally adjusting the distance of axes of said upper rollers from axes of said lower rollers.

19. The apparatus of claim 1 wherein said mold has an open bottom with a retaining flange extending radially inwardly from a inner periphery of the open bottom of the mold, and further comprises a mold bottom plate dimensioned to cover said open bottom of said mold, said mold bottom plate having a radially extending peripheral flange with a diameter sufficient to overlap said mold bottom retaining flange, said mold bottom plate having a thickness sufficient to rest flush with a bottom edge of the mold and to position said peripheral flange above said retaining flange when said mold and said mold bottom plate are resting on a flat surface, so that said peripheral flange of said mold bottom does not contact said retaining flange of said mold when said mold is gyrated.

20. A gyratory compactor apparatus for subjecting a material to forces, comprising:

a frame for supporting a mold, a mold carriage, a ram and a ram drive assembly, said mold having a mold cavity for receiving a quantity of said material, said mold further having an open top and a closed bottom, said ram positioned above said mold for axial insertion by said ram drive assembly into said mold cavity through said open top of said mold to compact said material in said mold cavity, and said mold carriage having lower rollers in contact with said mold and upper rollers positionable for rolling contact with a fixed ring portion of said frame, said fixed ring permanently attached at a fixed gyration angle relative to said frame, said mold carriage adjustable to orient a vertical axis of the mold at a fixed gyration angle, said mold carriage rotatable about said mold to gyrate said mold at said fixed gyration angle while said ram is inserted and driven into said mold cavity.

21. The gyratory compactor apparatus of claim 20 wherein said mold is in the form of a cylinder having a flange extending radially from an outer periphery of said cylinder, said flange being in contact with said lower rollers of said mold carriage.

22. The gyratory compactor apparatus of claim 20 wherein said closed bottom of said mold is comprised of a mold bottom plate having a radial peripheral flange which has a diameter sufficient to overlap a diameter of an annular lip of said mold extending radially inward about an inner periphery at the bottom of said mold.

23. The gyratory compactor apparatus of claim 20 wherein said ram and ram drive assembly are supported by a flexible portion of said frame which flexes in reaction to force transferred by said ram.

24. The gyratory compactor apparatus of claim 23 wherein said ram drive assembly comprises a lead screw in contact with a lead screw nut in contact with said ram.

25. The gyratory compactor apparatus of claim 24 wherein said ram drive assembly comprises a selectively controllable motor engaged to rotate said lead screw to linearly drive said ram.

26. The gyratory compactor apparatus of claim 25 further comprising means for electrically measuring an amount of flex of said flexible portion of said frame.

27. The gyratory compactor apparatus of claim 24 wherein said lead screw is journalled to rotate within thrust bearings, said thrust bearings being mounted within a block attached to said flexible portion of said frame.

28. The gyratory compactor apparatus of claim 26 further comprising a computer control system operatively connected to said ram drive assembly and to said flexible portion of said frame to receive measured values of flex of said flexible portion of said frame, whereby a rate of operation of said ram drive assembly is controlled by said computer control system according to said measurements.

29. The gyratory compactor apparatus of claim 20 further comprising a mold carriage tilt assembly connected to said frame and to said upper rollers of said mold carriage, said mold carriage tilt assembly operative to tilt and fix a center axis of a mold within said mold carriage so that it is not in alignment with a vertical axis of said ram.

30. The gyratory compactor apparatus of claim 20 further comprising means for powering rotation of said mold carriage about said mold, and means for electrically measuring an amount of power required to rotate said mold carriage about said mold while said ram is inserted and driven into said mold cavity.

31. A machine for applying a linear force by a ram comprising, in combination, a frame which supports a ram and a ram drive mechanism attached to said ram, said ram drive mechanism including a selectively controllable ram drive motor, said frame having a flexible portion which flexes in reaction to a force transferred by said ram, and means for measuring an amount of flex of said flexible portion of said frame when said flexible portion flexes in response to force transferred by said ram.

32. The machine of claim 31 wherein said ram drive mechanism includes a lead screw operative to induce linear movement of said ram by threaded engagement with a lead screw nut in contact with said ram, said lead screw journalled to rotate within bearings supported by said flexible portion of said frame.

33. The machine of claim 32 wherein said lead screw is rotationally driven by a belt driven gear attached to an end of said lead screw.

34. The machine of claim 33 wherein said belt is driven by contact with a gear connected to an output of an electric motor which serves as said ram drive motor.

35. The machine of claim 31 wherein said means for measuring an amount of flex of said flexible portion of said frame is a strain gauge in contact with said flexible portion.

36. The machine of claim 34 wherein said electric motor is a stepping motor, said stepping motor selectively controllable to apply a constant torque to said lead screw.

37. The machine of claim 34 wherein said electric motor is a stepping motor, said stepping motor selectively controllable to maintain a constant rotational speed of said lead screw.

38. The machine of claim 36 wherein said stepping motor is selectively controlled according to measured values of flex of said flexible portion as measured by a strain gauge, the output of said strain gauge input to a controller, said controller operative to control said motor in response to said measured values.

39. The machine of claim 31 wherein said ram drive motor is selectively controlled at least partially according to measurements of flex of said flexible portion of said frame.

40. A gyratory compactor apparatus for compacting a specimen of material while said specimen is gyrated, said apparatus comprising, in combination, a mold for holding said specimen, a mold support structure for supporting said mold, a compacting ram positioned and driven for insertion into said mold to compact said specimen within said mold, a mold gyrating assembly in contact with said mold and powered to gyrate said mold while said compacting ram is inserted and driven into said mold and, means for measuring an amount of power applied to said mold gyrating assembly to gyrate said mold while said ram is compacting said specimen within said mold.

41. The apparatus of claim 40 wherein said means for measuring an amount of power applied to said mold gyrating assembly is a watt meter.

42. The apparatus of claim 41 further comprising a computer control system operative to control and monitor said apparatus, wherein signals from said watt meter are supplied to the computer control system, and wherein the computer control system compensates said signal for precalibrated mechanical losses in the apparatus to provide an accurate reading of power applied to gyrate said mold by rotation of said mold gyrating assembly about said mold while said ram is compacting said specimen within said mold.

* * * * *